United States Patent [19]

Frenken et al.

[11] 4,254,297

[45] Mar. 3, 1981

[54] PROCESS FOR THE CONVERSION OF DIMETHYL ETHER

[75] Inventors: Petrus M. G. Frenken, Ed Thorn; Joseph J. F. Scholten, Sittard, both of Netherlands

[73] Assignee: Stamicarbon, B.V., Geleen, Netherlands

[21] Appl. No.: 98,117

[22] Filed: Nov. 27, 1979

[30] Foreign Application Priority Data

Nov. 30, 1978 [NL] Netherlands .......................... 7811732

[51] Int. Cl.$^3$ .............................................. C07C 1/00
[52] U.S. Cl. ..................................... 585/640; 585/733
[58] Field of Search ................................ 585/640, 733

[56] References Cited

U.S. PATENT DOCUMENTS

| | | | |
|---|---|---|---|
| 4,049,573 | 9/1977 | Kaeding | 252/432 |
| 4,072,732 | 2/1978 | Hargis et al. | 585/640 |
| 4,178,317 | 12/1979 | Horn et al. | 585/640 |

*Primary Examiner*—Curtis R. Davis
*Attorney, Agent, or Firm*—Cushman, Darby & Cushman

[57] ABSTRACT

Process for the conversion of dimethyl ether into a mixture of substantially aliphatic hydrocarbons and water by means of a catalyst containing boron. The dimethyl ether is put in contact, at a temperature of over 250° C., with a catalyst that consists of a crystalline modification of silica in whose crystal lattice a number of silicon atoms have been replaced by boron atoms.

The amount of boron in the crystalline modificaton, expressed as the molar ratio of the oxides $B_2O_3$ and $SiO_2$, may vary between 0.0005 and 0.025.

4 Claims, No Drawings

PROCESS FOR THE CONVERSION OF DIMETHYL ETHER

The invention relates to a process for the conversion of dimethyl ether into a mixture of substantially aliphatic hydrocarbons and water by means of a cyatalyst containing boron.

It is well known that dimethyl ether can be converted into a mixture of water and hydrocarbons with boiling points in the boiling range of the gasolines by passing dimethyl ether over a catalyst consisting of a crystalline aluminosilicate zeolite (see, e.g. U.S. Pat. No. 3,894,102). The hydrocarbons obtained in this conversion contain a high percentage of aromatics.

It is also known (see U.S. Pat. No. 4,049,573) to convert dimethyl ether into a mixture of hydrocarbons that contains not only aromatics, but also is rich in $C_2$ and $C_3$ olefins by passing dimethyl ether over a catalyst consisting of an aluminosilicate zeolite to which oxides of boron and/or magnesium and, optionally, of phosphorus have been added. The amount of boron oxide and/or magnesium oxide may vary between 0.25 and 25% by weight. As the percentage of oxides added increases, the yield of olefins is higher.

A new process has now been found for the conversion of dimethyl ether into a mixture of substantially aliphatic hydrocarbons and water by means of a catalyst containing boron.

The process according to the invention for the conversion of dimethyl ether into a mixture of substantially aliphatic hydrocarbons and water by means of a catalyst containing boron is characterized in that dimethyl ether is put in contact, at a temperature of over 250° C., with a catalyst containing boron that consists of a crystalline modification of silica in whose crystal lattice a number of silicon atoms have been replaced by boron atoms.

The amount of boron that has to be incorporated in the crystal lattice in order to effect a high conversion of the dimethyl ether amounts to 1-50 atoms of boron per 1000 molecules of silica. Expressed as a molar $B_2O_3$:$SiO_2$ ratio, these values are in the range 0.0005-0.025:1. Larger amounts of boron may also be used; but this does not result in an increase of the activity or selectivity of the catalyst and belongs to the object of the invention.

The temperature at which the conversion of dimethyl ether is effected may vary from 250° to 550° C.; the conversion is preferably effected at temperatures of between 350° and 500° C. The space velocity of the dimethyl ether normally ranges between 1.0 and 10 hour$^{-1}$. If so desired, the catalyst proper may be diluted with an inert material, such as alumina, silica and clay, or the catalyst may be pelleted or extruded.

The product obtained in the conversion contains water and also not inconsiderable amounts of aliphatic hydrocarbons, substantially propylene and butylenes, and only minor amounts of aromatics.

A suitable way of obtaining the crystalline modifications of silica and boron in a simple manner is the use of pure silica and a soluble boron compound as starting materials. Suitable boron compounds are boric acid, sodium borate, ammonium borate, soluble perborates and pyroborates and soluble organic boron compounds. In the preparation, pure silica dissolved in a tetraalkyl ammonium hydroxide is heated in an autoclave with a solution of a boron compound, the resulting crystalline product is removed from the autoclave, washed, dried and calcined while air is passed through. If, after the calcination, cations showing a non-acid reaction are still present, e.g. alkalimetal ions, the crystalline modification obtained is subjected to an ion exchange treatment with solutions that replace the cations in question by cations showing an acid reaction, such as hydrogen ions and/or ions of rare-earth metals and/or by ion groups that decompose upon heating, such as ammonium ions, while hydrogen is left on the surface. In the last case the crystalline modification that is subjected to ion exchange is heated again. As a result of the ion exchange, the crystalline modification acquires the completely catalytically active condition. Particularly good results are obtained if the starting material is amorphous silica, e.g. aerosil.

Suitable tetraalkyl ammonium hydroxides for the preparation are tetrapropyl and tetrabutyl ammonium hydroxide and mixtures thereof. Use may also be made of compounds that form these quaternary ammonium hydroxides under the reaction conditions, e.g. a mixture of a trialkyl amine with an alcohol or an alkyl halogenide. Furthermore, the autoclave must be made of, or be lined with, such a material that no elements of this material go into solution under the reaction conditions. A suitable material is Hastelloy C.

The catalyst has a micropore system, determined by the crystallography, whose pores have a uniform diameter. The organic nitrogen compounds have been removed from the pores by the calcination, so that these pores are accessible.

The conversion of dimethyl ether into a mixture of substantially aliphatic hydrocarbons and water by means of the catalyst described above will now be elucidated with reference to the examples, but without being restricted to them.

EXAMPLE 1

An amount of catalyst with a molar $B_2O_3/SiO_2$ ratio of 0.0027 (atomatic B/Si ratio=0.0054) was placed in a reactor. 8.88 grams of dimethyl ether were passed over the catalyst per hour at 400° C. and atmospheric pressure. The space velocity was 1.8 g/h per gram of catalyst. Upon termination of the experiment it was found that 98% of the starting material had been converted into other products.

Analysis of the resulting product gave the following result:

| | |
|---|---|
| methane: | 1% |
| ethane: | 0% |
| ethylene: | 3% |
| propane: | 1% |
| propylene: | 18% |
| butane: | 3% |
| butylenes: | 10% |
| $C_5$ and higher (non-aromatics): | 16% |
| benzene: | 0% |
| toluene: | 0% |
| $C_8$ aromatics: | 0% |
| $C_9$ aromatics: | 1% |
| $C_{10}$ and higher (aromatics): | 1% |
| methanol: | 6% |
| water: | 35% |

EXAMPLE 2

An amount of silica containing boron with a molar $B_2O_3/SiO_2$ ratio of 0.0044 (atomic B/Si ratio=0.0088) was placed in a reactor and 9.55 g of dimethyl ether was passed over it per hour at 500° C. and atmospheric pressure. The space velocity was 1.9 g/h per gram of catalyst. Upon termination of the experiment it was found that 89% of the starting material had been converted into other products.

Analysis of the reaction product gave the following result:

| | |
|---|---|
| methane: | 2% |
| ethane: | 2% |
| ethylene: | 2% |
| propane: | 0% |
| propylene: | 13% |
| butane: | 1% |
| butylenes: | 6% |
| $C_5$ and higher (non-aromatics): | 21% |
| benzene: | 1% |
| toluene: | 1% |
| $C_8$ aromatics: | 0% |
| $C_9$ aromatics: | 2% |
| $C_{10}$ and higher (aromatics): | 1% |
| methanol: | 8% |
| water: | 37% |

Both examples show that, by means of the above-described catalyst containing boron, dimethyl ether is converted into a mixture of substantially aliphatic hydrocarbons and water, said mixture containing only minor amounts of aromatic hydrocarbons.

We claim:

1. Process for the conversion of dimethyl ether into a mixture of substantially aliphatic hydrocarbons and water by means of a catalyst containing boron, characterized in that dimethyl ether is put in contact, at a temperature of over 250° C., with a catalyst containing boron that consists of a crystalline modification of silica in whose crystal lattice a number of silicon atoms have been replaced by boron atoms.

2. Process according to claim 1, characterized in that the amount of boron in the crystalline modification, expressed as the molar ratio of the oxides $B_2O_3$ and $SiO_2$, varies between 0.0005 and 0.025.

3. Process according to claims 1 or 2, characterized in that the conversion is effected at a temperature of between 250° and 550° C.

4. Process according to claims 1 or 3, characterized in that dimethyl ether is passed over the catalyst with a space velocity of between 1.0 and 10 $hour^{-1}$.

* * * * *